United States Patent [19]
Owens

[11] Patent Number: 5,598,923
[45] Date of Patent: Feb. 4, 1997

[54] STORAGE DEVICE FOR MOBILE MEDICAL APPARATUS

[76] Inventor: Susan S. Owens, 510 University Forest Dr., Conway, S.C. 29526

[21] Appl. No.: 508,897

[22] Filed: Jul. 28, 1995

[51] Int. Cl.$^6$ .............................. B65D 30/22; A45F 5/00
[52] U.S. Cl. .................... 206/370; 206/350; 206/438; 206/570; 206/818; 150/130; 248/206.5; 383/39; 383/119
[58] Field of Search .................... 206/370, 350, 206/818, 438, 570, 806; 248/206.5; 383/86, 39, 119; 150/130

[56] References Cited

U.S. PATENT DOCUMENTS

| | | |
|---|---|---|
| D. 334,588 | 4/1993 | Okala . |
| 1,984,122 | 1/1933 | Felmann .................... 150/130 |
| 3,181,751 | 5/1965 | Wilson ....................... 383/39 |
| 3,187,903 | 6/1965 | Oltz . |
| 3,749,237 | 7/1973 | Dorton ...................... 206/438 |
| 4,234,086 | 11/1980 | Dorton . |
| 4,301,916 | 11/1981 | Handelman .................. 383/39 |
| 4,605,292 | 8/1986 | McIntosh ................... 248/206.5 |
| 4,736,853 | 4/1988 | O'Mara ..................... 248/206.5 |
| 4,738,547 | 4/1988 | Brown ....................... 383/39 |
| 4,796,790 | 1/1989 | Hamilton .................... 206/570 |
| 4,949,843 | 8/1990 | Stokes . |
| 5,002,401 | 3/1991 | Blackman ................... 383/39 |
| 5,209,344 | 5/1993 | Smith . |
| 5,351,813 | 10/1994 | Golovan . |
| 5,363,953 | 11/1994 | Carter . |

FOREIGN PATENT DOCUMENTS 943342  3/1949  France .

Primary Examiner—Paul T. Sewell
Assistant Examiner—Luan K. Bui
Attorney, Agent, or Firm—Richard C. Litman

[57] ABSTRACT

A storage and display device comprises a magnetically attached storage unit which holds and displays personal protection supplies for use with, for example, a mobile X-ray machine. The storage and display apparatus includes two square opaque vinyl sheets, heat sealed to enclose a rigid, supporting cardboard insert; four fixed, symmetrical, translucent, pleated vinyl pockets; a protective, translucent, vinyl overlay with hook-and-loop (Velcro®) closures; and magnetic or hook-and-loop (Velcro®) mounting strips.

8 Claims, 2 Drawing Sheets

STORAGE DEVICE FOR MOBILE MEDICAL APPARATUS

BACKGROUND OF THE INVENTION

1. Field of the Invention

The present invention relates generally to storage apparatus, and more particularly to storage devices for use with health protection implements.

2. Description of the Prior Art

Considering the wide range of diseases to which healthcare workers are exposed, it is clearly important that healthcare workers have ready access to protective gear, such as gloves, caps, masks, etc. Numerous storage technologies have developed for this purpose, and others. However, no prior attempt provides easy accessibility and ready mounting as the present invention.

U.S. Pat. No. 3,187,903, issued to Charles R. Oltz, on Jun. 8, 1965, shows a rack construction having several connected storage pockets and two adhesive mounting strips. There is no showing of an over-lying cover.

U.S. Pat. No. 4,234,086, issued to Howard E. Dorton, on Nov. 18, 1980, shows a strip of bags each bag having three internal connections to prevent gaping of the bags. There is no showing of an over-lying cover.

U.S. Pat. No. 4,949,843, issued to William T. Stokes, on Aug. 21, 1990, shows a plurality of inter-connected pockets disposed in rows and columns. There is a mounting means at a top side of the plurality. There is no showing of an over-lying cover.

U.S. Pat. No. 5,209,344, issued to Dorothy A. Smith, on May 1, 1993, shows a plurality of inter-connected pockets disposed in rows and columns. There is a mounting means at a top side of the plurality. There is no showing of an over-lying cover.

U.S. Pat. No. 5,351,813, issued to Bruce Golovan, on Oct. 4, 1994, shows a plurality of individually releasable compartments disposed in rows and columns on a backing member. There is a mounting means on a back side of the mounting member. There is no showing of an over-lying cover.

U.S. Pat. No. 5,363,953, issued to Sandy Carter, on Nov. 15, 1994, shows a jewelry display having a mesh base. There are no pockets and there is no showing of an over-lying cover.

U.S. Design Patent No. Des. 334,588, issued to Frank Okala, on Apr. 6, 1993, shows a multiple file pocket folder. There is no showing of an over-lying cover.

French Patent Document No. 943,342, issued to Marco Penna, on Mar. 4, 1949, shows a plurality of individually releasable compartments disposed in rows and columns on a cardboard backing member. There is no showing of an over-lying cover.

None of the above inventions and patents, taken either singly or in combination, is seen to describe the instant invention as claimed.

SUMMARY OF THE INVENTION

A storage and display device according to the present invention comprises a magnetically attached storage unit which holds and displays personal protection supplies for use with a mobile X-ray or fluoroscopy machine. The storage and display apparatus includes two 18"×18" opaque vinyl sheets, heat sealed to enclose a rigid, supporting cardboard insert; four fixed, symmetrical, translucent, pleated vinyl pockets; a protective, translucent, vinyl overlay with hook-and-loop (Velcro®) closures; and magnetic mounting strips. Advantageously, the overlay protects against contamination of the protective gear, without creating difficulty in opening that individual pocket closures would create.

Accordingly, it is a principal object of the invention to provide a single overlay for multiple storage pockets.

It is another object of the invention to provide mounting means for mounting a storage device for protective gear on a mobile X-ray apparatus or fluoroscopy apparatus.

It is a further object of the invention to provide a stiffening mechanism for a primarily vinyl storage device.

Still another object of the invention is to provide a storage device that is simple in construction.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
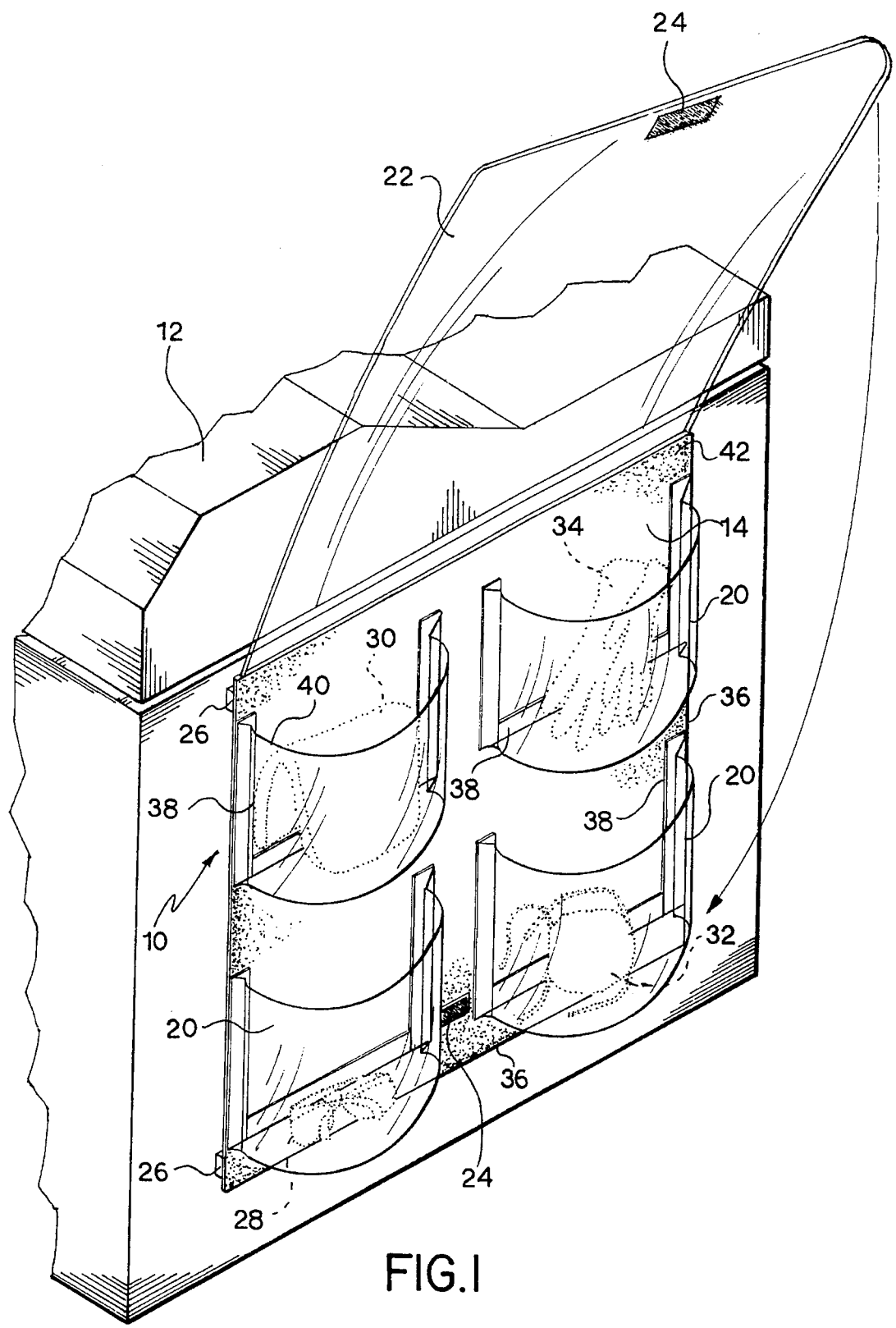
FIG. 1 is an environmental, perspective view of the present invention.
Figure 2:
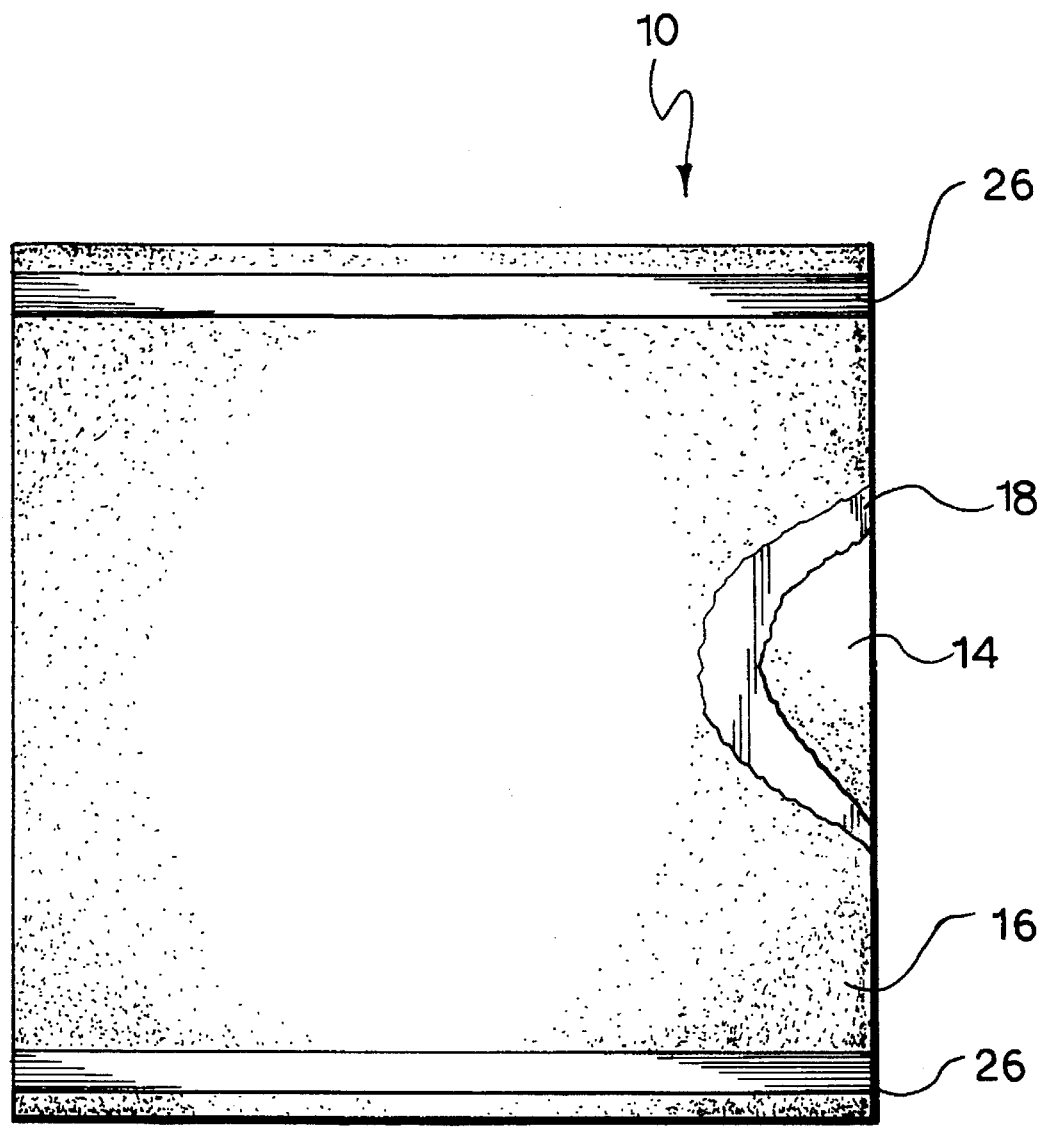
FIG. 2 is a rear partial cutaway view of the present invention, showing the mounting means and the internal cardboard stiffener.

The present invention provides convenient storage for use with such medical apparatus as mobile X-ray and fluoroscopy machines. Such storage is important because of the importance in health facilities of ready access to personal protective gear, such as gowns, gloves, goggles, and face masks. Such personal protective gear protects health care personnel from debilitating and lethal diseases. In order to remain effective, such gear must be kept free from contamination, as well as conveniently accessible. A storage device according to the present invention utilizes structural features that ensure both convenient access and contamination-free storage.

Referring to the drawings, a storage device 10 for mobile medical apparatus 12 according to the present invention comprises two covering sheets 14, 16, a stiffening member 18, four pocket sheets 20, an overlay 22 with closure means 24, and mounting means 26.

The covering sheets 14, 16 are preferably two 18"×18" opaque vinyl sheets, of an attention-attracting color, such as red. The color chosen should not lead to confusion with other devices used in health facilities. Optionally, the sheets 14, 16 could be light-transmissive, composed of different material, or configured to different dimensions. The covering sheets 14, 16 include a front covering sheet 14 and a back covering sheet 16.

The stiffening member 18 is planar and acts as a stiffening mechanism for a primarily soft vinyl storage device 10. Preferably, the stiffening member 18 is cardboard, although other materials could be used, such as plastic and light metal.

The four pocket sheets 20 are preferably symmetrical, light-transmissive, pleated vinyl sheets, although other materials could be used. Additionally, more or fewer sheets 20 could be used.

The overlay 22 is a protective, light-transmissive, vinyl sheet, preferably with hook-and-loop (Velcro®) closures 24, although other overlay closure means could be used, such as a snap, a button, a latch, and other conventional closure means. The overlay 22 is dimensioned and configured to substantially and selectively cover the pocket sheets 20. Advantageously, the overlay 22 protects against contamination of the protective gear 28, 30, 32, 34, without creating difficulty in opening that individual pocket closures would create. That is to say, according to the present invention, there is a single overlay 22 for protecting contents of multiple storage pockets 20.

The mounting means 26 is preferably a pair of elongated magnetic mounting strips 26, when the mounting means 26 is used for mounting the storage device 10 for protective gear 28, 30, 32, 34, on a mobile X-ray apparatus 12. For this mounting means 26, the X-ray apparatus 12 must be susceptible to magnetic attraction. Alternately, the mounting means 26 is mating hook-and-loop fasteners. This mounting means 26 is preferred for use when mounting the storage device 10 on a fluoroscopy apparatus, in which there are no metal surfaces susceptible to magnetic attraction.

The storage device 10 of the present invention is simple in construction. Edges 36 of the covering sheets 14, 16 are preferably heat sealed to one-another to enclose the stiffening member 18 between the covering sheets 14, 16. Other conventional sealing techniques could be used. The pocket sheets 20 are preferably heat sealed at three edges 38 to the front covering sheet 14 in a suitable arrangement, such as in rows and columns. Other conventional sealing techniques could be used. Heat sealing of the pocket sheets 20 is accomplished in such a manner as to ensure that a pocket 20 open at a top edge 40 is formed, i.e. there is volume between the heat-sealed pocket sheets 20 and the front covering sheet 14, except at edges 38 of the pocket sheets 20 where the actual sealing occurs. The overlay 22 is preferably heat sealed to the front covering sheet 14 across a top edge 42 of the front covering sheet 14. Other conventional sealing techniques could be used. The closure means 24 and mounting means 26 are then attached by known means to the front covering sheet 14 and the back covering sheet 16, respectively.

Use of the storage device 10 is also simple. The mounting means 26 is oriented toward a medical apparatus 12 to which the storage device 10 is to be attached. Orientation is accomplished in such a way that unsealed edges 40 of the pocket sheets 20 are directed upwards toward the top edge 42 of the front covering sheet 14. Then the storage device 10 is mounted on the medical apparatus 12, and the overlay closure 24 is released. The overlay 22 is lifted and appropriate protective gear 28, 30, 32, 34 is inserted between the pocket sheets 20 and the front covering sheet 14. Such protective gear 28, 30, 32, 34 can include goggles 28, gowns 30, face masks 32, and gloves 34. The overlay 22 is closed and the overlay closure 24 is then re-fastened to protect against contamination of protective gear 28, 30, 32, 34. When a user desires to use stored protective gear 28, 30, 32, 34, the closure member 24 is released and the overlay 22 is lifted. Access to the desired protective gear 28, 30, 32, 34 is immediate. The user need not go to a different area of a health facility to search for the protective gear 28, 30, 32, 34. Moreover, the user need not hassle with multiple, small compartment lids, but instead need only open a single, large, easy to grip overlay 22.

It is to be understood that the present invention is not limited to the sole embodiment described above, but encompasses any and all embodiments within the scope of the following claims.

I claim:

1. A storage device for holding and displaying medical protective gear, said storage device comprising:

a back opaque vinyl covering sheet having edges;

a front opaque vinyl covering sheet having edges, said edges of said back covering sheet being heat sealed to said edges of said front covering sheet;

a rigid planar stiffening member disposed between said back covering sheet and said front covering sheet;

a plurality of transparent pocket sheets, each of said transparent pocket sheets heat sealed to said front covering sheet, said transparent pocket sheets being dimensioned and configured to form open pockets;

a transparent vinyl overlay heat sealed to a top edge of said front covering sheet, said overlay dimensioned and configured to cover said transparent pocket sheets and having overlay closure means provided on the overlay for releasably fastening the lower portion of the overlay to the lower portion of the storage device;

mounting means for attaching the storage device to a mobile medical apparatus, said mounting means disposed on said back covering sheet.

2. The storage device according to claim 1 wherein said overlay includes, an overlay closure means provided on said overlay whereby said overlay is releasably connected to said front covering sheet.

3. The storage device according to claim 1, wherein said mounting means is a pair of elongated magnetic strips.

4. The storage device according to claim 1, wherein said mounting means is a pair of elongated hook-and-loop fasteners.

5. The storage device according to claim 1, wherein said stiffening member is cardboard.

6. The storage device according to claim 1, wherein said plurality of pocket sheets is light-transmissive vinyl material.

7. The storage device according to claim 2, wherein said closure means is a hook-and-loop fastening.

8. A storage device for holding and displaying medical protective gear, said storage device comprising:

a back covering sheet having edges;

a front covering sheet having edges, said edges of said back covering sheet being heat sealed to said edges of said front covering sheet, said front covering member and said back covering member are opaque vinyl material;

a rigid planar stiffening member disposed between said back covering sheet and said front covering sheet, said stiffening member being cardboard;

a plurality of transparent pocket sheets, each of said transparent pocket sheets heat sealed to said front covering sheet, said plurality of pocket transparent sheets being dimensioned and configured to form open pockets, said plurality of transparent pocket sheets being light-transmissive vinyl material;

an overlay heat sealed to a top edge of said front covering sheet, said overlay being dimensioned and configured to substantially and selectively cover said pocket sheets, said overlay being light-transmissive vinyl material;

an overlay closure means provided on said overlay whereby said overlay is releasably connected to said front covering sheet, said overlay closure means is a hook-and-loop fastening; and a mounting means disposed on said back covering sheet, said mounting means being selected from a pair of elongated magnetic strips and a pair of elongated hook-and-loop fasteners.

* * * * *